United States Patent
Cyrus et al.

[11] Patent Number: 5,891,049
[45] Date of Patent: Apr. 6, 1999

[54] TIME AND DATA CORRELATED MEDICAL DISPLAY SYSTEM

[75] Inventors: Judith L. Cyrus, Preston; Garry R. Gordon; Clinton S. Cole, both of Issaquah; Justin Grimley; Leona Bell, both of Seattle, all of Wash.

[73] Assignee: Heartstream, Inc, Seattle, Wash.

[21] Appl. No.: 987,193

[22] Filed: Dec. 8, 1997

Related U.S. Application Data

[60] Division of Ser. No. 648,778, May 16, 1996, Pat. No. 5,785,043, which is a continuation-in-part of Ser. No. 314,395, Sep. 28, 1994, Pat. No. 5,549,115.

[51] Int. Cl.$^6$ .................................................. A61B 5/432
[52] U.S. Cl. ............................................................. 600/523
[58] Field of Search ................................... 128/898, 920; 600/523

[56] References Cited

U.S. PATENT DOCUMENTS

| | | |
|---|---|---|
| 3,853,119 | 12/1974 | Peterson et al. . |
| 4,006,737 | 2/1977 | Cherry . |
| 4,250,888 | 2/1981 | Grosskopf . |
| 4,483,346 | 11/1984 | Slavin ...................................... 600/523 |
| 4,610,254 | 9/1986 | Morgan et al. . |
| 4,715,385 | 12/1987 | Cudahy et al. . |
| 4,945,477 | 7/1990 | Edwards . |
| 5,002,062 | 3/1991 | Suzuki . |
| 5,086,778 | 2/1992 | Mueller et al. . |
| 5,228,450 | 7/1993 | Sellers . |
| 5,277,188 | 1/1994 | Selker . |
| 5,333,616 | 8/1994 | Mills et al. . |
| 5,334,030 | 8/1994 | Brilliott . |
| 5,338,210 | 8/1994 | Beckham et al. . |
| 5,345,367 | 9/1994 | Pierce et al. . |
| 5,538,006 | 7/1996 | Heim et al. .............................. 600/523 |

FOREIGN PATENT DOCUMENTS

| | | |
|---|---|---|
| 3 221 399 A1 | 12/1983 | Germany . |
| 4 337 110 C1 | 11/1994 | Germany . |
| 06 036098 A | 2/1994 | Japan . |
| 2 225 495 | 5/1990 | United Kingdom . |

OTHER PUBLICATIONS

Brochure, Advanced EMS Defibrillators from ZOLL.

Operating instructions for Laerdal Heartstart Medical Control Unit with Multiplex Tape Format.

Operating instructions for Laerdal Heartstart Database Manager 3.3 (1991).

Marquette® Responder™ 1500 Defibrillator and cardiac care system operator's manual (16th Ed.) (1994).

Physio Control ECG/Voice Translator Operating Instructions.

Physio Control Code–Stat™ data management system User Guide (1996).

*Primary Examiner*—William E. Kamm

[57] ABSTRACT

A method for displaying time-correlated medical event data including the steps of: providing time-correlated event data to a display device; selecting a first event to be displayed; and displaying the first event together with a time-correlated second event on the display device. In another embodiment, the invention is a method for displaying time-correlated medical event data including the steps of: manually entering data comprising a first event into a display device; time-correlating the first event with data comprising a second event collected by a medical device; and displaying the first event together with the second event on the display device. In yet another embodiment, the invention is a method of creating a report showing the time correlation between recorded medical events, the method comprising the steps of: connecting a memory device to a display device, the memory device comprising a clock; retrieving event data and time data from a memory device; reading a memory device time from the memory device clock; and using the memory device time to associate time with the event data.

1 Claim, 8 Drawing Sheets

TIME AND DATA CORRELATED MEDICAL DISPLAY SYSTEM

This application is a divisional of U.S. patent application Ser. No. 08/648,778, filed May 16, 1996 now U.S. Pat. No. 5,785,043, which is a continuation-in-part of U.S. patent application Ser. No. 08/314,395, filed Sep. 28, 1994, now U.S. Pat. No. 5,549,115.

FIELD OF THE INVENTION

The present invention relates in general to a system and method for presenting time-correlated medical event data gathered and recorded by a medical device, such as during an emergency medical response, and, more particularly, presenting data as a set of randomly accessible events.

BACKGROUND OF THE INVENTION

Electrotherapy devices are used to provide electric shocks to treat patients for a variety of heart arrhythmias. For example, external defibrillators provide relatively high-energy shocks to a patient, usually through electrodes attached to the patient's torso, to convert ventricular fibrillation to a normal sinus rhythm. Similarly, external cardioverters can be used to provide shocks to convert atrial fibrillation to a more normal heart rhythm. In this application, the term "electrotherapy device" includes devices performing only a monitoring function.

Event data means information that can be related to particular intervals of time. The time intervals may be "elapsed time," i.e., time related to a reference event, such as power-up of the data collecting device or start of the data collection process. The time intervals may instead be synchronized with a master standard, such as Greenwich mean time or an arbitrarily selected timekeeper, in which case the time is known as "synchronized time." Accepted time units (seconds, minutes, etc.) are used to measure both elapsed time and synchronized time.

One example of event data is an electrocardiograph showing a patient's heart electrical activity, which may be plotted versus elapsed time from a starting or triggering event. Event data also includes the raw data upon which the plots or graphs are based, whether in digital, analog or any other form. The event data may be a continuous data stream, a discontinuous series of events, or a combination of continuous data and discrete events.

Prior art electrotherapy devices record event information and time information collected from the patient, reported by the device and/or otherwise collected from the devices' surroundings (such as audio information, including the voices of the devices' operators) during the operation of the device. This and other information collected by an electrotherapy device may be referred to collectively as "electrotherapy information". For example, the Laerdal Heartstart 3000 external defibrillator records patient ECG and information about the defibrillator in a solid state memory module. This patient and ECG information can be later retrieved from the memory module using suitable software. As another example, the Marquette Responder 1500 external defibrillator stores event data such as patient ECG on a data card inserted into a data card slot in the defibrillator. The event and time data regarding the patient's physiological condition may be logged to provide information to later caregivers about the patient and about the care the patient received, such as the time required for the emergency medical technicians to reach the patient and the patient's response to the treatment.

Event data collected from electrotherapy devices may be analyzed to extract useful time-based information. Part of the event data analysis often requires reference to a local clock by the data user to place the time stamped on the collected event in the context of the data user's time. For example, if a portion of the collected event indicates that the event occurred at 4:00 PM, the data user must assume that the electrotherapy device clock and the data user's local clock indicated "4:00 PM" at the same time. In other words, the data user must assume that the electrotherapy device clock and the data user's local clock are synchronized. In addition, the data user must assume that the electrotherapy device's measure of a second or a minute is the same as the data user's local measure of a second or a minute so that the recorded time (whether elapsed time or synchronized time) may be interpreted in a meaningful way.

The synchronized time indicated by a device's clock may drift from the synchronized time indicated by the master timekeeper because of environmental conditions, mechanical problems, or other reasons. Also, the act of setting the electrotherapy device clock could introduce discrepancies between the time indicated by the device's clock and the time indicated by the data user's clock, especially if the data logger clock is set by hand, or if the electrotherapy device's clock was not initially synchronized to the data user's clock prior to event data collection. These problems are compounded if a single data user receives event data from multiple electrotherapy devices, since each electrotherapy device clock may have been affected in different ways by environmental conditions, errors in initial setting, and the like. Thus, when the accurate logging of synchronized time is important, a relatively expensive clock and elaborate and/or expensive time setting procedures may have to be included in the electrotherapy device.

When emergency response personnel are called to the scene of a cardiac arrest, a report of the incident is desirable from several standpoints. First, many jurisdictions require emergency response personnel to file such incident reports, detailing the condition of the patient and the type of treatment delivered. Second, from the standpoint of accurate diagnosis and subsequent treatment, it is desirable to note the various treatments applied at the scene and record the patient's response. Such information might help trained cardiologists, sitting in review of the incident, to rule out certain disease or defect conditions that potentially afflict the patient.

Paramedics and other emergency medical response personnel are often the first on the scene and are usually sent out to the patient from a central dispatch in response to a "911" call or other emergency calling service. These personnel typically carry portable external defibrillators to treat patients suffering from sudden cardiac arrest. Most currently available portable defibrillators have some means for collecting and storing information concerning the patients and the type of treatment delivered to the patient. For example, prior art defibrillators record the patient's ECG as well as the conversation of the response personnel and other sounds of the incident in progress.

Much of the information, however, is recorded in incident reports that are generated and compiled manually by the response personnel after rendering treatment at the scene. Additionally, the presentation of compiled data does not allow for a robust means of identifying and accessing particular data that occurred at particular points in time (called "events"). U.S. Pat. No. 4,610,254 to Morgan et al. discloses a portable interactive defibrillator that records patient status information such as ECG as well as usersupplied information that is input in the form of prompts from the defibrillator to the user. Morgan further discloses the use of a tape recorder medium to record relevant medical information during the use of device. The recorder is a two-track recorder—one track for ECG and other patient data and the second track for audio data to record the voice of the response personnel as well as sounds indicating that a shock has been delivered to the patient.

U.S. Pat. No. 4,945,477 to Edwards discloses a system for recording and presenting information pertaining to a medical event such a cardiac arrest. Edwards' system records events identified by the defibrillator and stores these events for human-readable replay. Defibrillator-identified events (termed "annotations") can be effected by the pressing of a button on the defibrillator by the user or by the recognition that a medical event (e.g., arrhythmia) has occurred. As a memory space saving technique, Edwards describes a means in which his system stores three second intervals according to priority of events. Events having higher priority may well overwrite events of lower priority.

U.S. Pat. No. 5,277,188 to Selker discloses a clinical information reporting system that inputs both ECG-related and non-ECG-related (e.g. laboratory test results such as blood enzymes, urinalysis, blood pressure, and the like) patient cardiac data into a database. Selker's database maintains such data for a group of patients, typically admitted at a health care facility. Information stored in the database allows a user to classify patients into meaningful clinical classes and generate reports concerning the process of care for cardiac patients.

While these systems do provide some level of data recording and play-back, they do not provide a full range of event identification and presentation that would be useful for trained medical personnel to quickly assess an individual patient's condition, particularly soon after a cardiac arrest. For example, in a recorded 10–20 minute emergency response, instead of requiring a reviewing cardiologist to view the entire response to get to the events of interest, it would be useful for the cardiologist to "jump" directly to certain events (e.g. times where shock has been administered to the patient). Additionally, it would be useful for trained personnel to manually identify and annotate certain points in time as events—particularly for events that would not necessarily be automatically recorded by the device (e.g., the time when certain drugs have been administered to the patient).

Thus, it is an object of the present invention to provide medical personnel with a system that quickly and accurately allows random access to events that occurred during the course of an emergency response.

It is another object of the present invention to allow users to manually input and annotate events that occur during a response and have those manually-input events randomly accessible during playback.

SUMMARY OF THE INVENTION

The present invention is a novel apparatus and method for recording and replaying patient treatment and response data that occurs during the course of an emergency response. The data and events of an emergency response may be recorded automatically by the present apparatus or may be recorded manually by a user—either during the course of the emergency or anytime thereafter.

The present invention records "events" that occur during the course of the emergency response. These events may be recorded during the emergency automatically by the device or entered manually thereafter by users. Events may then be named and displayed as a "list" to trained medical personnel who are reviewing the response. Events may then be randomly accessible or selectable (i.e., "scrollable") by medical personnel. The ability to scroll through "events", as opposed to being required to playback an entire response as it occurred chronologically, provides a fast and efficient method to allow medical personnel access to the most pertinent data to effect an accurate diagnosis of the patient.

One advantage of the present invention is efficiency. As noted above, the ability to scroll through "events", as opposed to a chronological presentation of the response, gives medical personnel flexibility in data retrieval for a more timely diagnosis of the patient. This is particularly important for immediate follow-up treatment of a patient admitted to an emergency room of a hospital where time is of the essence in delivering effective treatment.

In one embodiment, the invention is a method for displaying time-correlated medical event data including the steps of: providing time-correlated event data to a display device; selecting a first event to be displayed; and displaying the first event together with a time-correlated second event on the display device. The providing step could include connecting a memory device to the display device. The providing step could also include using the display device to collect time-correlated event data or, alternatively, providing time-correlated event data collected by a medical device and providing user-entered event data, with the method further comprising correlating the user-entered event data with time-correlated event data collected by the medical device.

In one embodiment, the second event is patient ECG data, with the displaying step including displaying the first event together with at least a portion of the ECG data correlating in time with the first event. The displaying step could also include displaying a marker together with the patient ECG data, the marker representing the first event. The marker could be a caption.

In another embodiment of the method of this invention, the selecting step includes selecting the first event from a list of events, such as from a list of events displayed on the display device. Alternatively, the selecting step could include entering a unique identification of the first event into the display device.

In a preferred embodiment, the providing step comprises providing time-correlated event data collected by a defibrillator, the second event comprising patient ECG data. The first event could be delivery of a shock by the defibrillator to a patient. In addition, the providing step could include providing time-stamped event data and correlating the time-stamped event data.

In another embodiment, the invention is a method for displaying time-correlated medical event data including the steps of: manually entering data comprising a first event into a display device; time-correlating the first event with data comprising a second event collected by a medical device; and displaying the first event together with the second event on the display device. The method could include creating a list comprising a first entry corresponding to the first event and, possible, selecting the first entry from the list prior to the displaying step.

In another embodiment, the invention is a method of creating a report showing the time correlation between recorded medical events, the method comprising the steps of: connecting a memory device to a display device, the memory device comprising a clock; retrieving event data and time data from a memory device; reading a memory device time from the memory device clock; and using the memory device time to associate time with the event data. The invention could also include reading a display device time from a display device clock and using the display device time to associate time with the event data. The event data and time data may correlate a plurality of events, with the retrieving step comprising retrieving a correlating factor (such as a number of event records) for the event data from the memory device.

In yet another embodiment, the invention is a method of assembling a database of time-correlated medical event data including the following steps: gathering medical event data using an electrotherapy device, the medical event data comprising a plurality of data points corresponding to a first category of medical event (such as patient ECG) and a plurality of data points corresponding to a second category of medical event; correlating a data point from the plurality of data points corresponding to the first category of medical event with time; correlating the plurality of data points corresponding to the second category of medical event with the plurality of data points corresponding to the first category of medical event; and storing both pluralities of data points and their correlation information. The method could include the step of building a time-correlated event file from the pluralities of data points and their correlation information. The method could also include the step of displaying the pluralities of data points in a time-correlated manner.

Finally, in another embodiment the invention is a medical display system including a digital memory, the digital memory containing a database comprising a plurality of data points corresponding to a first category of medical event and a plurality of data points corresponding to a second category of medical event and correlation information time-correlating the first and second pluralities of data points; and means for displaying the pluralities of data points in a time-correlated manner.

Other advantages and features of the present invention will become apparent from the following detailed description as illustrated in the accompanying figures.

DETAILED DESCRIPTION OF THE INVENTION

The following is presented to enable any person skilled in the art to make and use the invention. Various modifications to the preferred embodiment will be readily apparent to those skilled in the art, and the generic principles defined herein may be applied to other embodiments and applications without departing from the spirit and scope of the present invention as defined by the appended claims. Thus, the present invention is not intended to be limited to the embodiment shown, but is to be accorded the widest scope consistent with the principles and features disclosed herein.

Figure 1:
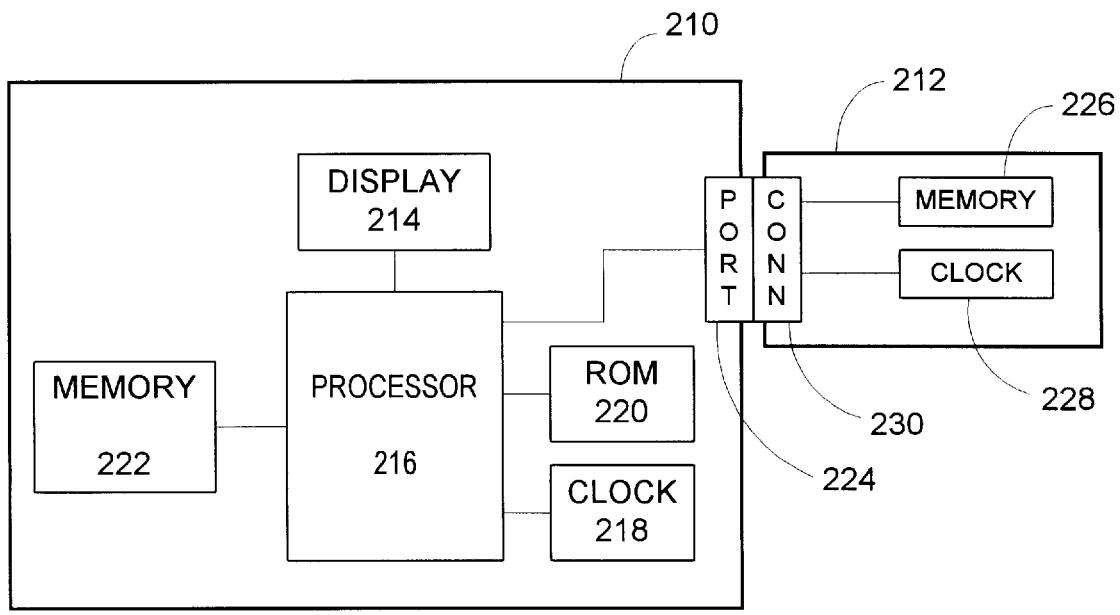
FIG. 1 is a block diagram showing a medical data display device to which a attachable/detachable memory device has been connected.

FIG. 1 is a block diagram showing a medical data display device 210 to which an attachable/detachable memory device 212 has been connected. In the preferred embodiment, display device 210 is a microprocessor-based PC running Microsoft Windows 3.x or higher attached to a suitable monitor or display 214. Display device 210 may also be a personal computer running some other operating system or a specially-dedicated microprocessor-controlled display device providing a graphical display and user interface. Display device 210 includes a microprocessor 216, clock 218, system ROM 220, memory 222, and external memory port 224, to which attachable/detachable memory device 212 has been connected, as shown.

Memory device 212 contains time-correlated medical event data gathered by a medical device. The event data and time information is stored in digital form in digital memory 226 in memory device 212. In the preferred embodiment, the time information stored within digital memory 226 is taken from a clock 228 within memory device 212. Memory device 212 communicates with the external memory port 224 of display device 210 through a connector 230.

In alternative embodiments, the time-correlated medical event data can be provided to the display device remotely through a modem connection, an Ethernet connection, a wireless connection, etc., in a manner known in the art.

Once the medical event data and time information are provided to the display device, the data and information can be manipulated and displayed in a useful form. The following discussion describes the use of the invention to manipulate and display time-correlated event data gathered by an semi-automatic external defibrillator. It should be understood that the invention can be used to manipulate and display other medical event information as well.

External defibrillators are electrotherapy devices used to treat victims of sudden cardiac arrest. They deliver an electrical shock to the patient's heart through electrodes attached to the patient's body to convert a the unorganized rhythm of a fibrillating heart to an organized heart rhythm.

External defibrillators are often operated by trained medical personnel who are dispatched to the scene of a sudden cardiac arrest to treat the patient. Information about the patient gathered by the defibrillator itself and by the medical personnel can be valuable for later caregivers. In addition, information about the response time of the medical personnel (such as time between dispatch and treatment, time between treatments, result of treatments, etc.) can be valuable in evaluating the overall effectiveness of an emergency medical response system.

In a preferred embodiment, the invention provides a method and apparatus for manipulating and displaying time-correlated defibrillator event data in a format called an incident report. An incident report contains event data relating to the treatment of a single patient by an emergency medical response team using an external defibrillator.

Figure 2:
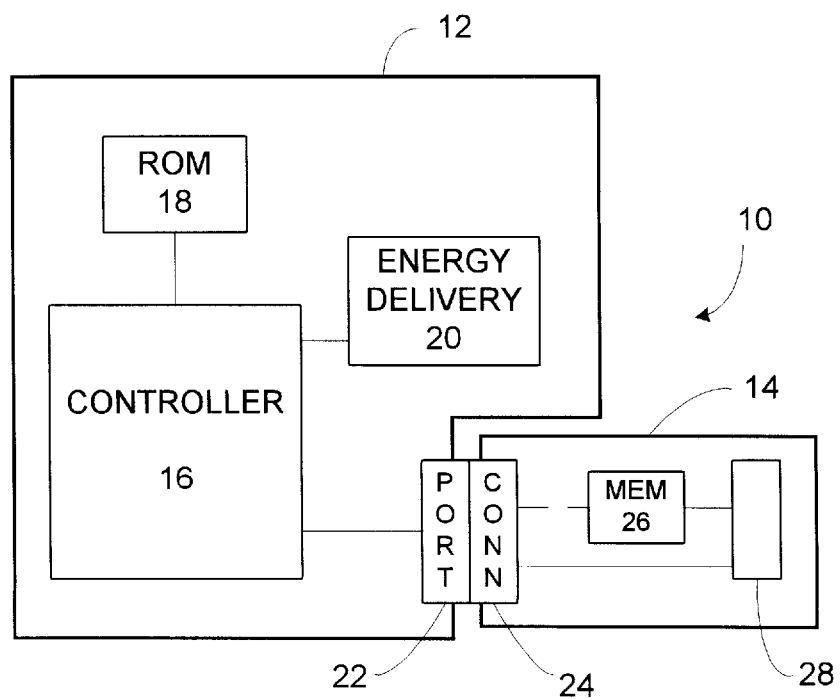
FIG. 2 is a block diagram showing an electrotherapy system useful for gathering event data for use with the invention.

FIG. 2 is a block diagram of an electrotherapy system according to one embodiment of this invention. Electrotherapy system 10 includes an electrotherapy device 12 connected to a memory device 14. Electrotherapy device 12 may be an external defibrillator, an external cardioverter, an external pacer, or any other electrotherapy device. A controller 16 within electrotherapy device 12 operates the device according to software instructions contained within device ROM (Read Only Memory) 18. It should be understood that, in this and other embodiments described below, "controller" means a microprocessor, controller, gate array, other control logic, or any combination of these elements.

The electrotherapy device operating modes can include patient treatment (in which, e.g., a therapeutic pulse is delivered to a patient via energy delivery and monitoring module 20), monitoring (in which, e.g., the patient's ECG is monitored through module 20) and self-test mode (in which device 12 runs self-test procedures to determine its operating condition). In any of its operating modes, electrotherapy device 12 can communicate event data with memory device 14 via memory port 22, which communicates with a digital memory 26 within memory device 14 via a connector 24. Electrotherapy device 12 also communicates with a clock 28 in memory device 14 through connector 24. Clock 28 provides time information for association with the event data from electrotherapy device 12, as discussed below.

During operation in patient treatment mode, electrotherapy device 12 may collect event information relating to the patient (such as patient ECG) and event information relating to the device itself (such as the charging of energy delivery and monitoring module in preparation for a shock or the delivery of the shock itself). Controller 16 transmits this event information to digital memory 26 in memory device 14. In addition, controller 16 associates time information taken from clock 28 with the event data and stores the associated time information in digital memory 26 as well.

During operation in monitoring mode, electrotherapy device 12 may collect and record patient information and its associated time without providing any treatment to the patient. The electrotherapy device may also record device event information and its associated time as well.

During operation in self-test mode, electrotherapy device 12 performs self-test and/or self-calibration procedures either automatically or on demand. Further information on self-test and calibration procedures for electrotherapy devices may be found in copending U.S. patent application Ser. No. 08/240,272, "Defibrillator With Self-Test Features," filed May 10, 1994, the disclosure of which is incorporated herein by reference. The controller may store the results of the self-tests and/or calibrations in digital memory 26 along with associated time information taken from clock 28.

Event data collected by the electrotherapy device 12 and stored in memory device 14 may be used later in a location, such as a hospital, which is physically distant from the initial treatment location. Memory device 14 can be separated from electrotherapy device 12 and connected to a main data recovery unit (such as a computer) in the hospital or other location through appropriate connectors. In this way, the event data is available for later diagnosis and treatment, and the electrotherapy device itself remains available for use in the field.

The clock 28 used by the electrotherapy device to associate time information with the ECG, defibrillator operating condition, and/or other event data will be connected to the main data recovery unit along with the digital memory. This step permits a comparison between the clock 28 and a main clock within the main data recovery unit so that the electrotherapy device event data can be associated with synchronized time. This comparison can be used to determine whether synchronized time indicated by the memory device clock (i.e., the time associated with the recorded event data) differs from the synchronized time standard shown by the main data recovery unit. In addition the ability to connect the memory device clock and the main clock permits time synchronization of the electrotherapy device prior to use in the field and correction for any clock drift after use in the field through interpolation or any other known technique. Furthermore, this system permits multiple electrotherapy devices to synchronize their clocks with a single main clock and to transfer or copy their collected event data into a single data recovery unit. The event data gathered by each will eventually be recovered in a single place and will be synchronized to a single time source.

In an alternative embodiment, a clock within the electrotherapy device is used together with clock 28 to associate time information with the electrotherapy event data.

Each electrotherapy device may uniquely identify the data it gathers so that the main data recovery unit will be able to distinguish event data gathered from one instrument from other event data. This data identification may be done in any manner known in the art.

This invention can be used to learn valuable information regarding emergency medical response times. Since the memory device clock used with each electrotherapy device is each synchronized to the clock in the main data recovery unit, the main data recovery unit can accurately calculate the time between dispatch (if the dispatch clock is synchronized to the main data recovery unit clock) and use of the electrotherapy device to treat a patient. The calculated response times for each electrotherapy device can be accurately compared, since each electrotherapy device clock is synchronized to the same recovery unit clock. The invention also eliminates the need for a technician to periodically set a reference time source (such as his or her watch) from the main clock and visit all of the remote electrotherapy device sites in order to keep all of the instrument clocks in the system synchronized.

Preferred embodiments of this invention are described below with reference to external defibrillators. It should be understood that the invention also relates to other electrotherapy devices as well.

Figure 3:
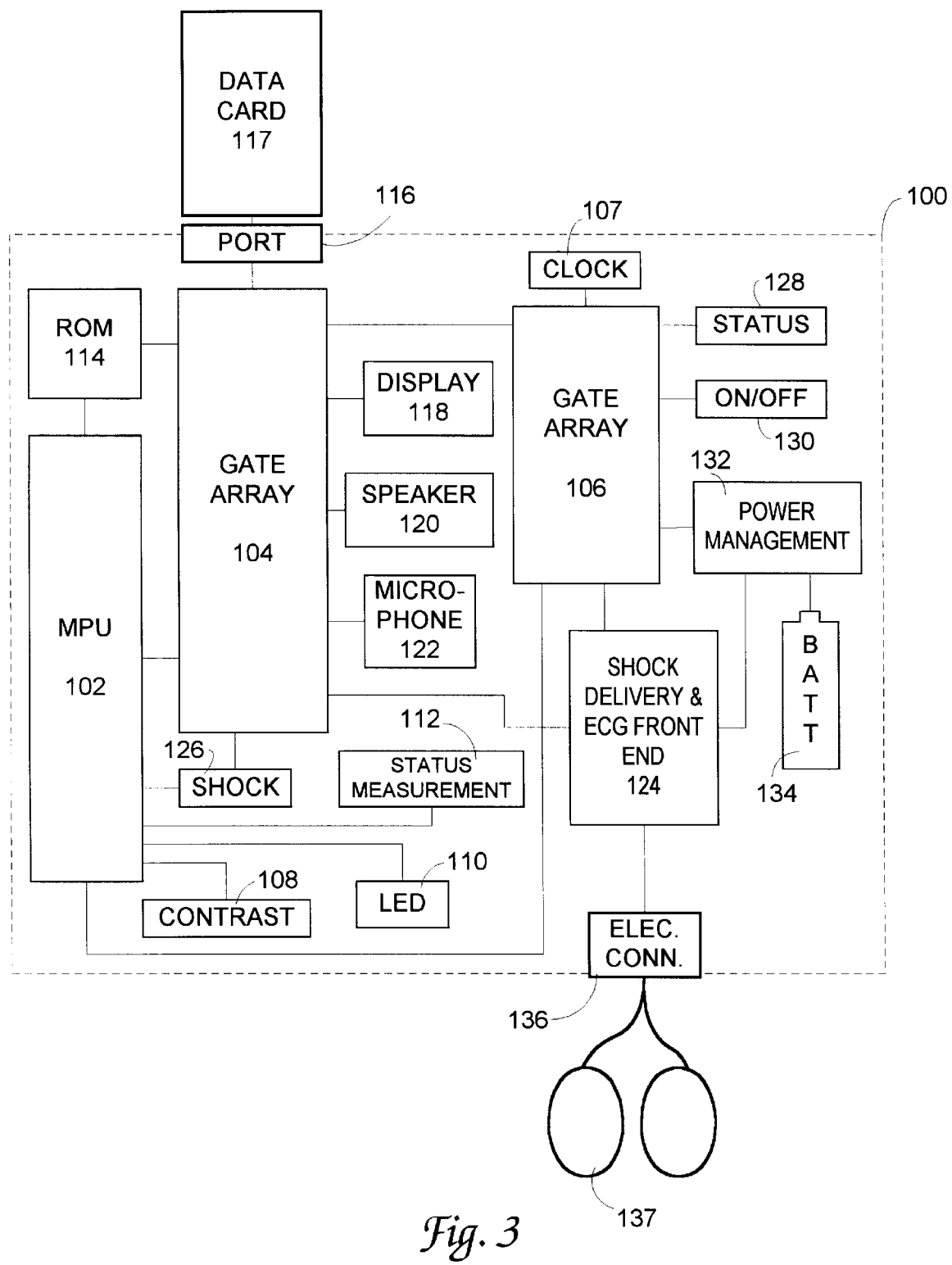
FIG. 3 is a block diagram of an external defibrillator useful for gathering event data for use with the invention.

The major components of a semi-automatic external defibrillator according to a preferred embodiment are shown in FIG. 3 in block diagram form. Defibrillator control functions are divided among a microprocessor unit (MPU) 102 and two custom gate arrays 104 and 106. It should be understood, however, that gate arrays 104 and 106 are optional, and their functions can be performed by other circuits.

MPU 102 performs program steps according to software instructions provided to it from ROM 114. MPU 102 controls the operation of certain buttons (such as display contrast buttons 108) and certain system LED's 110 (such as LED's associated with the shock button and the electrode connector). MPU 102 also receives system status information as shown by block 112.

Gate array 104 implements the memory map to system ROM 114, data card port 116 and other system memory elements. System ROM 114 is preferably flash ROM, although EPROM or any other electrically erasable and programmable nonvolatile memory could be used. Data card port 116 is preferably a data card slot configured to interface with PC data cards conforming to the 1995 PC Card standard.

For purposes of writing to a data card, gate array 104 provides the interface and control between defibrillator 100 and a data card 117 attached to data card port 116. For example, gate array 104 contains a FIFO buffer to compensate for differences between the speed with which ROM 114 can be accessed by MPU 102 and the speed with which the memory portion of data card 117 can be accessed. Gate array 104 also controls a display 118, a speaker 120, and a microphone 122. Gate array 104 can actuate a relay within the shock delivery and ECG front end system 124 in response to actuation of a shock button 126 by a user during treatment mode.

Gate array 106 receives time information from clock 107. Gate array 106 also provides a system monitor function by performing automatic self-tests of the defibrillator and its components. The gate array 106 displays the operational status of the defibrillator on a status display 128. Details of suitable self-tests may be found in copending U.S. patent application Ser. No. 08/240,272, "Defibrillator With Self-Test Features," filed May 10, 1994, the disclosure of which is incorporated herein by reference. The results of the self-tests may be stored as time-correlated event data in system memory and/or in data card 117. Gate array 106 is also the defibrillator's interface with a user-activated on/off switch 130.

Gate array 106 controls the power management subsystem 132 to provide power to operate system components from battery 134 and to provide energy to the shock delivery system's capacitor(s) for a therapeutic shock during treatment mode. Gate array 106 also interfaces with the defibrillator's ECG front end 124, enables the shock delivery system to deliver a shock in response to detection of a patient ECG pattern requiring treatment (and actuation of the shock button), and controls delivery of the shock to electrode connector 136 in response to shock delivery status information obtained during delivery of the shock. Further information regarding this last function may be found in copending U.S. Pat. No. 5,735,879 "Electrotherapy Method for External Defibrillators," issued Apr. 7, 1998, and U.S. Pat. No. 5,607,454, "Electrotherapy Method and Apparatus," issued Mar. 4, 1998, the disclosures of which are incorporated herein by reference.

These defibrillator components communicate with each other over suitable communication buses, as shown.

Figure 4:
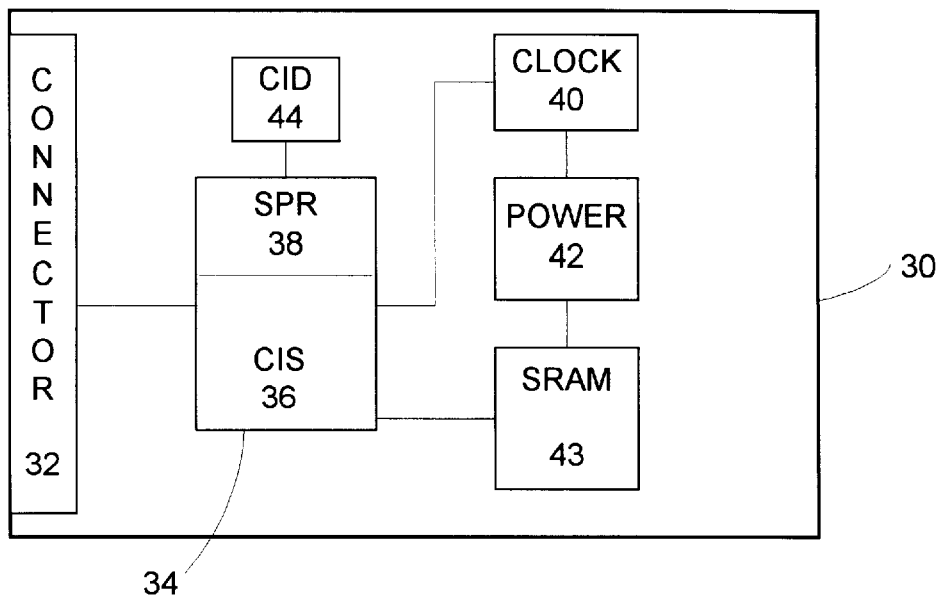
FIGS. 4 and 5 show suitable data cards for use with the invention.
Figure 5:
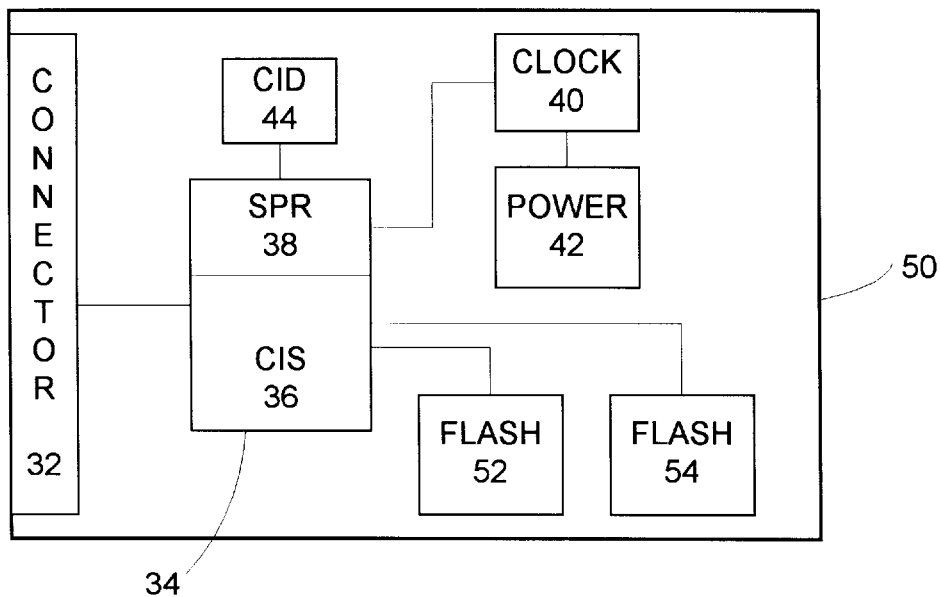

FIGS. 4 and 5 show suitable patient data cards for use with the defibrillator shown in FIG. 3. Data cards 30 and 50 are preferably in the 1995 PC Card standard format, with two key changes from the 1995 PC Card guidelines, as discussed below. It should be understood, however, that other digital memory formats may be used, such as the Minicard format promoted by Intel, Microsoft and others.

Data cards 30 and 50 each have a card connector 32 communicating with a gate array 34 over suitable buses. Gate array 34 contains the data card's Card Information Structure (CIS) 36 following the attribute memory of the 1995 PC Card guidelines. In addition, however, gate array 34 contains eight special purpose registers (SPR) 38.

Seven of the SPR 38 communicate with a clock 40, such as the elapsed time counter (ETC) chip clock 40 DS 1602, available from Dallas Semiconductor. Clock 40 preferably has a 32-bit elapsed-time counter which begins counting when power is first provided to the clock's battery back-up pin from on-card battery 42 (i.e., when the card is first assembled). The counter increments once each second. Battery 42 is preferably a lithium battery.

One of the SPR 38 communicates with the card identification (CID) source 44. CID 44 provides information about the card, such as type of memory on the card, size of memory on the card, data format, presence or absence of readable data (such as executable code), etc.

Data cards 30 and 50 differ in the kind of digital memory they provide. Data card 30 has an SRAM chip 43, while data card 50 has two substantially identical FLASH memory chips 52 and 54. Other combinations of memory, and other kinds of electrically erasable and programmable memory, are within the scope of the invention.

Figure 6:
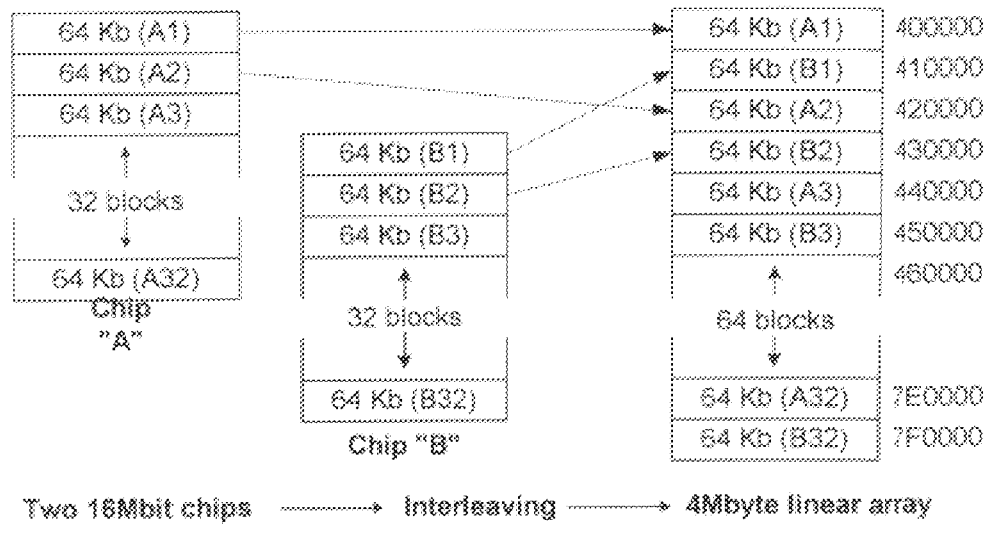
FIG. 6 shows an interleaving memory scheme for memory in a data card.

In the case of data card 50, both memory chips 52 and 54 are either top boot or bottom boot chips, although this is not necessary. In the preferred embodiment, the FLASH memory array is interleaved in a unique way to support an erase-on-the-fly scheme in a linear memory array. For example, for 16 Mbit chips having 32 64 Kbyte erase blocks, no data may be written to any block if another block in that chip is currently being erased. Since a block erase can take several seconds, an erase-on-the-fly scheme would require write suspends of up to several seconds each time a new block in the same chip is erased. To overcome this situation while preserving a linear memory array, data card 50 uses two 16 Mbit chips to form a 4 Mbyte linear array with interleaved 64 Kbyte blocks, i.e., the first 64 Kbyte block in a linear memory map is in one 16 Mbit chip (e.g., chip 52), the next is in the other chip (54), and so on. Thus, an application may erase a 64 Kbyte block immediately ahead of the one currently being accessed. FIG. 6 illustrates this scheme.

External defibrillator 100 can be operated in different modes, such as self-test mode, stand-by mode and patient treatment mode. Operation of the external defibrillator of this embodiment commences with the insertion of a battery. Once gate array 106 determines that a battery has been inserted to provide power to the defibrillator, gate array 104 prompts MPU 102 to begin its boot sequence. The boot sequence begins with MPU 102 sending out a series of addresses to gate array 104. Unless given instructions to the contrary, the initial MPU addresses to gate array 104 lead MPU to system ROM 114 for the remaining boot sequence.

The defibrillator's initial operation mode when booting from system ROM 114 is self-test mode during which the defibrillator performs an array of self-tests responding to insertion of the battery and possibly to the passage of time or an environmental event. Successful performance of these self-tests places the defibrillator in stand-by mode. The battery insertion self-tests may be terminated before completion by actuating on/off button 130, in which case the defibrillator's displayed status is determined by a shortened self-test sequence.

In stand-by mode, gate array 106 monitors for the presence of system power, the passage of time, temperature or other criteria. Gate array 106 places the defibrillator back into self-test mode when dictated by the passage of a suitable length of time, environmental conditions or other criteria. Failure of a self-test may cause the gate array 106 to place the defibrillator in an inoperable mode, in which case gate array indicates the inoperable status of the defibrillator through status display 128 and possibly other means. As stated above, the self-test results may be stored as time-correlated event data in system memory and/or in data card 117. In addition, environmental conditions—whether or not they trigger a self-test—may be recorded as event data as well.

When defibrillator 100 is in stand-by mode, actuation of on/off button 130 causes MPU 104 to begin receiving instructions from system ROM 114 to operate the defibrillator in a mode dictated by the instructions present in ROM 114. For example, provided that suitable instructions are present in ROM 114, actuation of on/off button 130 will place defibrillator 100 in patient treatment mode after successful completion of the defibrillator's power-on self-tests.

In patient treatment mode, defibrillator 100 can (1) determine whether electrodes 137 are attached to electrode connector 136, (2) receive ECG information from a patient through such electrodes, (3) analyze the ECG information to determine whether a therapeutic shock is advised, and (4) deliver a shock to the patient through the electrodes if a shock is advised and if the shock button 126 is actuated by a user. Defibrillator 100 can also store information regarding the patient (such as ECG information), the defibrillator (such as defibrillator operation information) and other information (such as ambient sounds received by microphone 122) on a patient data card attached to data card port 116.

In the preferred embodiment, time information corresponding to all recorded event data comes from (1) defibrillator clock 107 and/or (2) the clock on the data card or other memory device. The following discussion illustrates the correlation of time information with event data collected during patient treatment mode. The invention covers the recording and time-correlation of other event data as well.

The event data collected by an external defibrillator (such as the defibrillator of FIG. 3) in patient treatment mode according to a preferred embodiment of this invention include the following: defibrillator power on; defibrillation pads on or off; patient ECG; artifact detection; shock advised; no shock advised; charge begun; charge complete; device armed; device disarmed; shock initiated; shock delivered; shock aborted; pause for CPR; pause ended; manual override; manual charge; manual timeout; device off; low battery; depleted battery; critical error detected; non-critical error detected; audio (e.g., voice). The defibrillator obtains time information from the defibrillator clock and/or the clock on the memory device and stores the time information with the event data.

As a specific example, when using the defibrillator of FIG. 3 and one of the data cards of FIGS. 4 or 5 to record this information and to provide the time information, the recording process begins when the defibrillator is turned on. At this time, the defibrillator records in data card digital memory (SRAM 43 or FLASH 52 or 54) a "device on" time from the continuous counter in clock 40. At the same time, the defibrillator starts a software counter associated with clock 107. In a new use of the data card (i.e., when data begins recording at the beginning of the data card), ECG data is recorded after defibrillation electrodes or pads are attached to the patient and existing ECG memory on the card is erased. When the first ECG data point is recorded, a "record time" (derived from the software counter) is written to the data card memory. The ECG data is recorded and stored in data card memory at a resolution of 200 data points per second.

With the exception of audio (e.g., voice) data, which start prior to ECG collection, all event data stored in data card memory are correlated with the ECG data point associated most closely with it in time. This technique provides finer correlation between ECG and other event data than the data card clock (with a resolution of only 1 sec.) can provide. The correspondence of the event data to clock time can easily be computed.

After the defibrillator has been used to treat a patient and the time-correlated event data has been recorded, the memory device (e.g., data card) can be detached from the defibrillator and transported to a main data recovery unit (such as a PC). The clock on the data card will permit synchronization of the time-correlated event data with a clock in the main data recovery unit.

Figure 7:
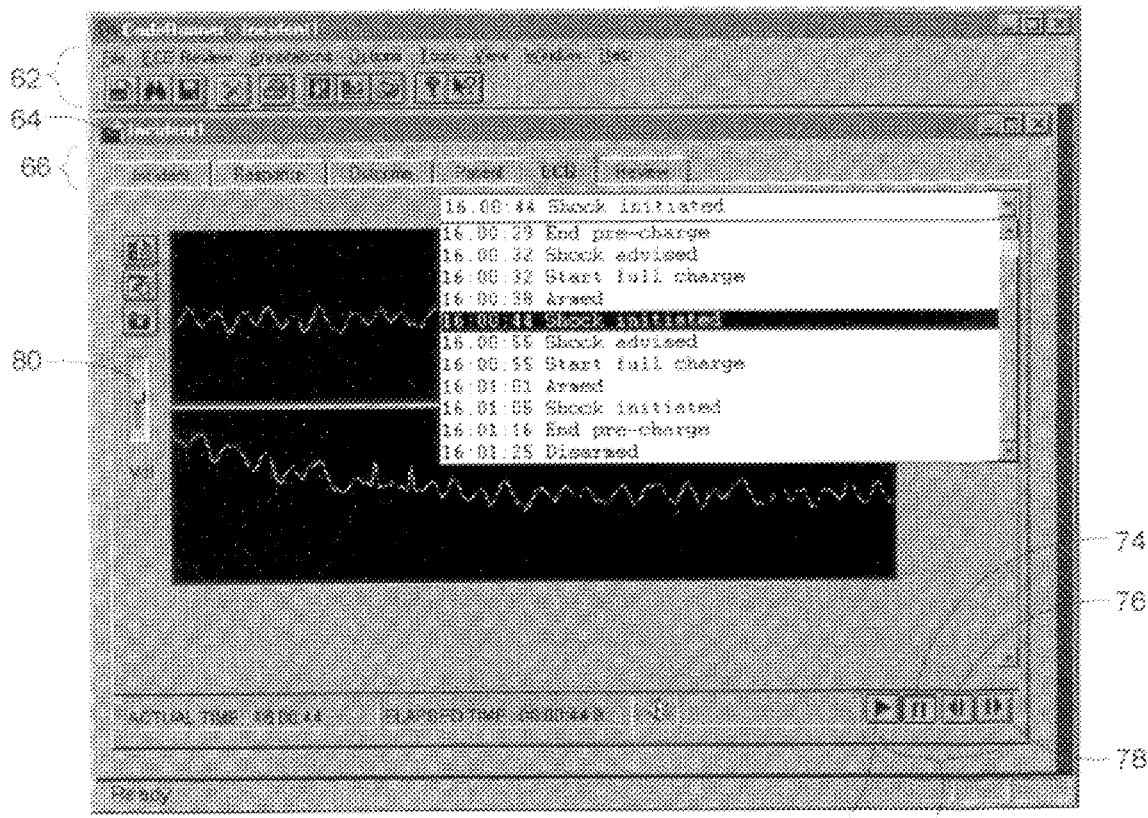
FIG. 7 is a graphical user screen interface that depicts a "pull-down" menu operation of the Event and Annotation List.

FIG. 7 is a graphical user screen interface that comports with the teaching of the present invention. Screen 60 is depicted as a Windows-like display having all the features therein. A main menu bar 62 contains the major commands to access a database of incident reports or to add such reports to the database. Available commands allow you to OPEN an incident database (i.e., load the response data from an incident and give access to the display program), CREATE a new incident for entry to the database, SAVE an incident, PRINT an incident, DISPLAY and PRINT an array of reports, TRANSFER an incident from an attached memory device (such as a PC card) to a file on a floppy disk, DELETE an incident, or SEND an incident to another site via modem. One such incident, Incident1, is opened in FIG. 7.

The Incident child-window 64 itself has several "TABs" 66 which provides access into different views of the data associated with an incident. INCIDENT displays or allows entry of data associated with the time and location of an incident, RESPONSE displays or allows entry of data associated with the response time and initial incident assessment, OUTCOME displays or allows entry of data associated with the patient's condition and transport at the end of the incident, PATIENT displays or allows entry of patient identification information, ECG displays the ECG and events recorded by the recording device and displays or allows entry of events and annotations by a reviewer, REVIEW displays or allows entry of data regarding assessment of the incident, patient follow-up information and reviewer identification. On the right hand side of child-window 64, scroll bar 68 and VCR-type buttons 70 (comprising PLAY 72, STOP 74, REWIND 76, and FAST FORWARD 78) control the relative spatial and temporal display of the data respectively. On the left hand side of child-window 64, volume control 80 controls the level of volume of the recorded, accompanying audio of the incident.

EVENT SCROLLING

Figure 8:
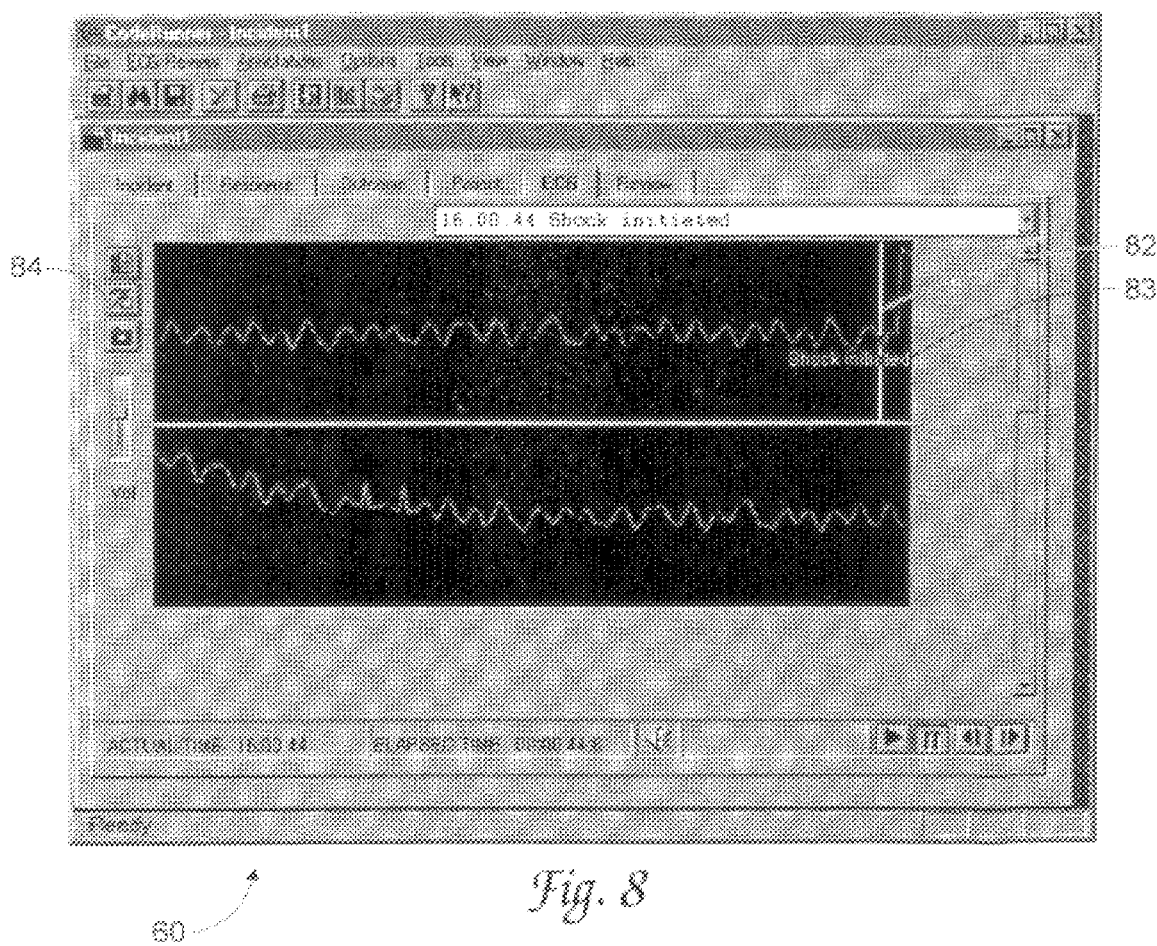
FIG. 8 is the screen interface that results after selecting and scrolling to the "Shock Initiated" Event that is shown in FIG. 7.

FIGS. 7 and 8 depict a "drop-down" list operation that may be performed on child-window 64. The user sets the input focus to the Events and Annotations list 81 provided in child-window 64. The user can then use the up and down arrow keys on a keyboard to navigate forward and backwards through the list of events and annotations. The user may also use a mouse to pull down the list, and scroll through the list and select any of the items in the list.

Each time a different event is selected by the user (e.g., "16:00:44 Shock initiated"), the ECG display is immediately changed to display the strip of ECG that contains the selected event item. A sweepbar 82 is displayed at the selected event to give a visual cue to where the audio playback is relative to the ECG. This placement of the sweepbar is a convenience allowing the user to start playback of the audio from the new location in the ECG. If the user then selects the PLAY button 72 (optionally accompanied by the recorded audio track), sweepbar 82 scans the ECG data in "real-time". Also shown in FIG. 8, text annotation 83 is placed in the ECG display to provide yet another visual cue to aid in data interpretation.

USER-DEFINED "EVENTS"

The annotation feature of the present invention allows the user to place several pre-defined as well as user-defined "events" into the ECG display. The present invention, by default, displays all the events recorded by device 10 in the same display as the ECG data. All annotations that are either automatically placed (such as New or Continued Use; Defibrillation Pads On or Off; Artifact Detected; Shock Advised; No Shock Advised, Charge Begun; Charge Complete; Device Armed; Device Disarmed; Shock Initiated; Shock Delivered; Shock Aborted; Pause for CPR; Pause Ended; Manual Override; Manual Charge; Manual Timeout; Device Off; Low Battery; Depleted Battery; Critical Error Detected; Non-Critical Error Detected) or manually placed into the Event and Annotation list can be used for future navigational purposes.

Figure 9:
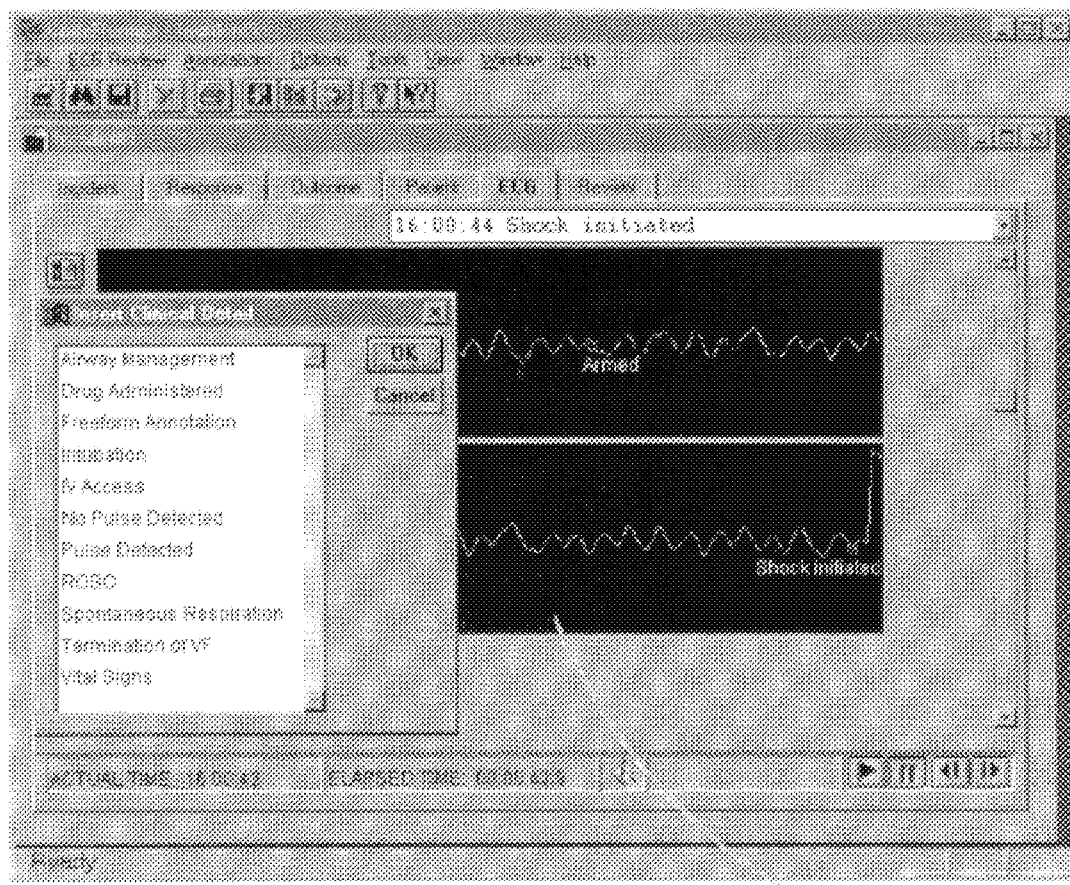
FIGS. 9 and 10 are screen interfaces that depict the manner in which events are stored and annotated in memory for later replay.
Figure 10:
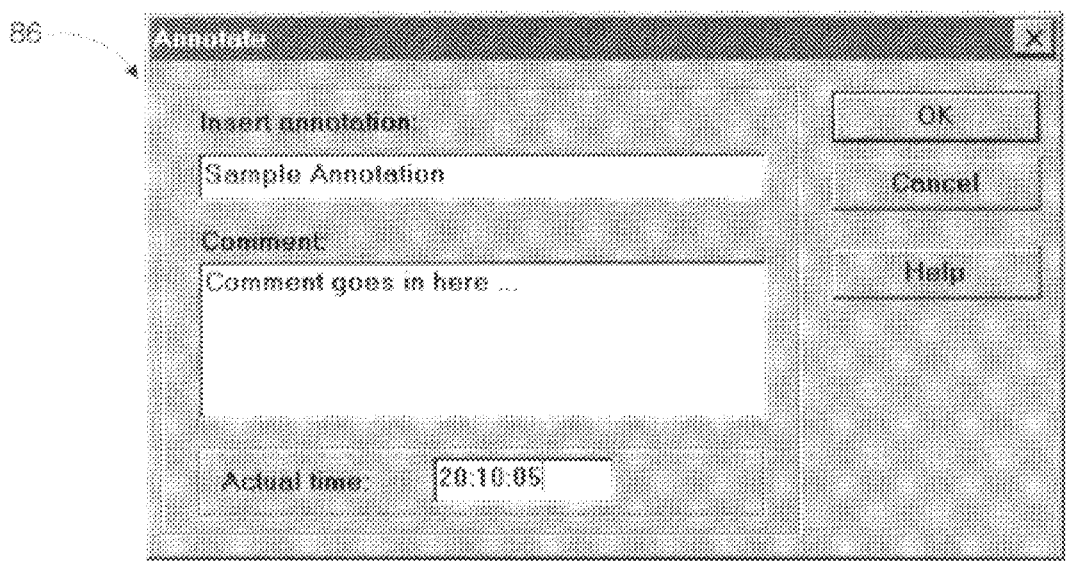
Figure 11:
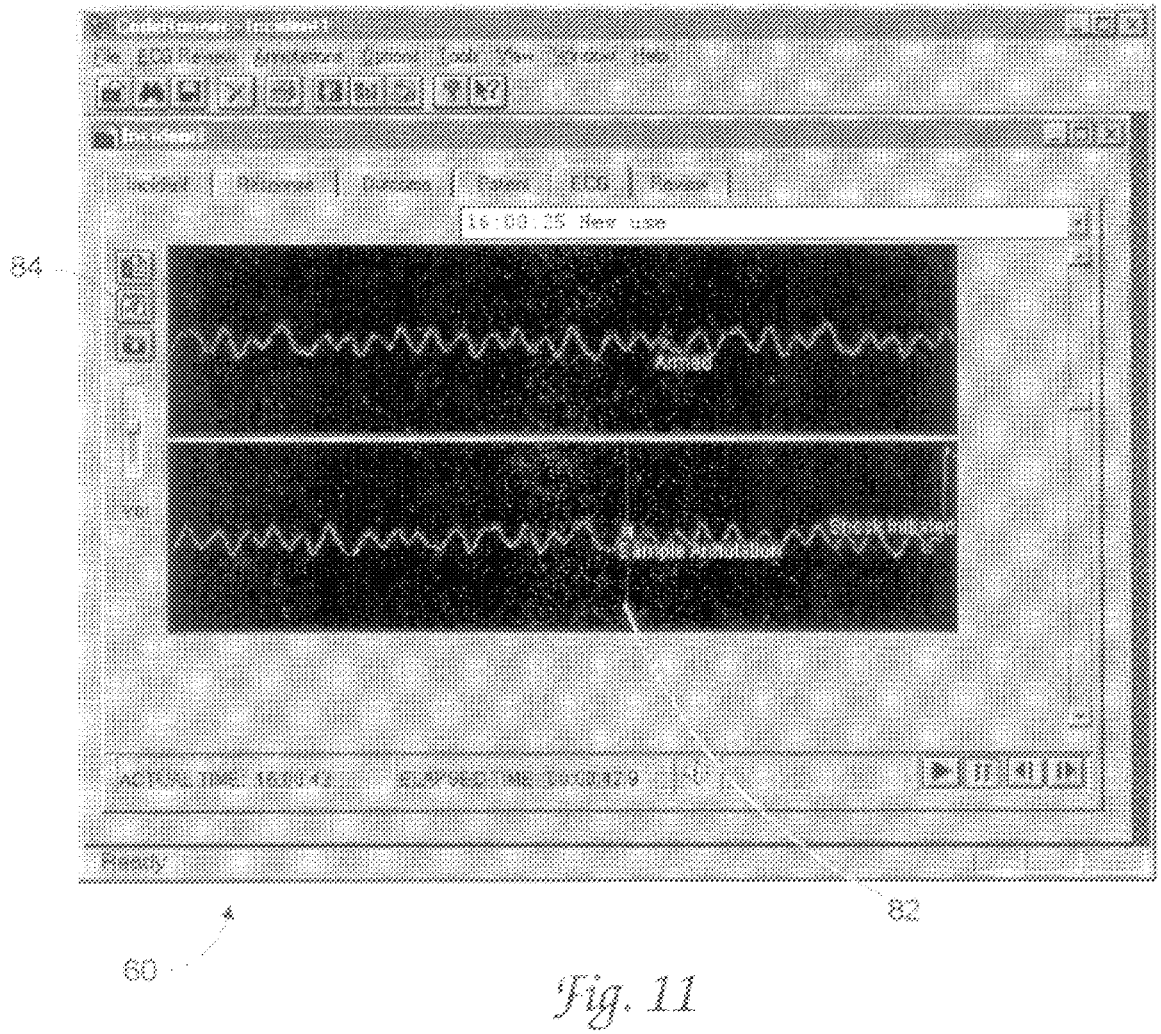
FIG. 11 depicts the visual display of a new event after its creation.

In reference to FIGS. 9, 10 and 11, to use the annotation feature, the user selects the annotation icon 84 in the ECG display which will display a dialog containing the Annotation list. At this point, the user would begin the playback of the audio portion. Once the playback has commenced, sweepbar 82 will move across the strip of ECG data, scrolling the strips as necessary. At any time, the user may select an annotation from the list (e.g., by "double clicking" on one of the items). Once selected the audio playback pauses and sweepbar 82 stops moving. A dialog box 86 is also presented to the user prompting for more information relative to the type of annotation selected.

Once the user has completed entering in the relevant data, the user confirms the annotation by selecting OK. This will insert the annotation so that the caption for the annotation appears in the ECG display (as shown in FIG. 11) and in the Events and Annotations list, resumes the audio playback, and resumes sweepbar 82 motion across the strip.

DATA CARD TIME-STAMPING

As previously mentioned, time synchronization of electrotherapy event data can be important. The following discussion describes a preferred way of correlating event data with time information.

Figure 12:
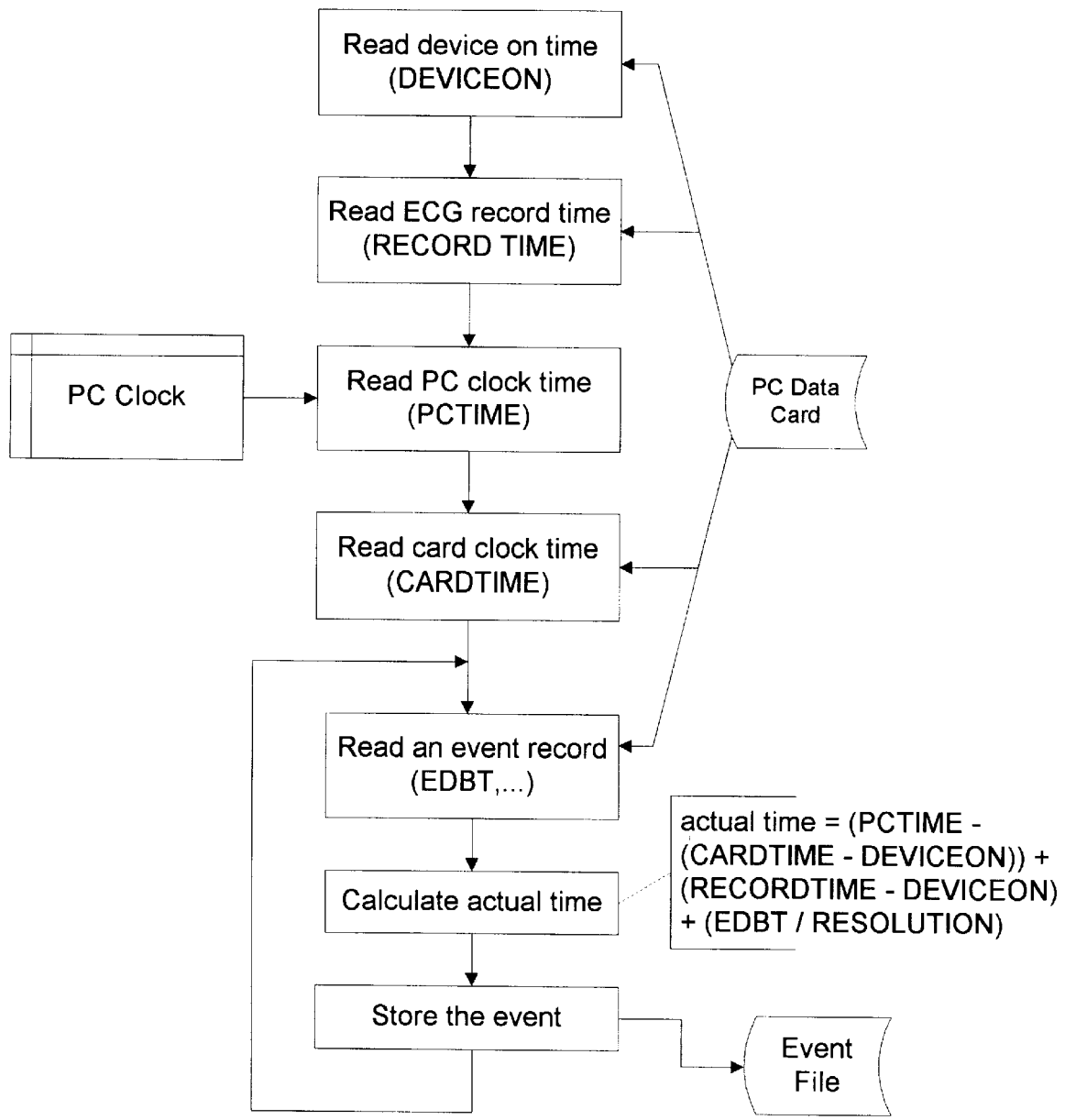
FIG. 12 is a flow chart that shows the manner in which time synchronization occurs for accurate data storage.

FIG. 12 is a flow chart that shows the manner in which time synchronization occurs in one embodiment of the present invention using the defibrillator of FIG. 3 and a data card according to FIG. 4 or 5. As discussed above, the act of turning on the defibrillator records a time from the clock (elapsed time counter) in the data card. This time is DEVICEON. Defibrillator power-on also starts the defibriliator's software counter.

At the time that the first ECG value is gathered from the patient and recorded on the data card, the defibrillator stores a time RECORDTIME, which is the sum of DEVICEON and the time shown on the defibrillator's software counter.

In one embodiment, the ECG is recorded at a rate of 200 Hz, and each ECG data point is assigned an ECG Display Buffer Time (EDBT) number starting with 0 for the first ECG data point. Other events (except for audio, which is recorded using a separate buffer time) are tagged with the current EDBT value at the time the particular event is recorded.

After the data has been collected by the defibrillator, the data card may be transferred to a main data recovery unit, such as a PC. The event data time recorded on the data card can be correlated with the time shown on the PC clock by following the method shown in FIG. 12.

To assemble an event file for the stored electrotherapy event data, the PC uses the stored DEVICEON and RECORDTIME values, the current time CARDTIME shown in the data card clock, and the current time PCTIME shown on the PC's clock. Then, for each ECG and other event record tied to the EDBT, the actual time associated with that event can be calculated as follows:

Actual Time=(PCTIME−(CARDTIME−DEVICEON))+(RECORDTIME−DEVICEON)+(EDBT/RESOLUTION)

where RESOLUTION is defined as the sampling rate for the ECG, in this case, 200/second.

The conversion of this time into day, month, year, hours, minutes and seconds is performed through various runtime library routines available through DOS and Windows APIs. After the actual local time is computed, this value is then stored and associated with the data item.

The actual time computed in this manner can be synchronized with another clock (such as an emergency medical dispatch clock) by simply synchronizing the PC clock with the other clock.

Modifications to the invention will be apparent to those skilled in the art. For example, time-of-day clocks can be used in place of the elapsed time counters described in the preferred embodiments.

What is claimed is:

1. A medical display system comprising:
    a digital memory, the digital memory containing a database comprising a plurality of data points corresponding to a first category of medical event and a plurality of data points corresponding to a second category of medical event wherein the first and second pluralities of data points are time-correlated; and
    a display device for displaying the plurality of data points in a time-correlated manner.

* * * * *